United States Patent
Beeckman et al.

(10) Patent No.: US 7,326,818 B2
(45) Date of Patent: Feb. 5, 2008

(54) SELECTIVATION OF MOLECULAR SIEVE CATALYSTS AND USE THEROF IN HYDROCARBON CONVERSION

(75) Inventors: Jean W. Beeckman, Columbia, MD (US); William G. Borghard, Haddon Heights, NJ (US); Arthur W. Chester, Cherry Hill, NJ (US); Robert A. Crane, Lumberton, TX (US); Owen C. Feeley, Lebanon, NJ (US); John C. Fried, Easton, PA (US); Dominick N. Mazzone, Wenonah, NJ (US); Glenn R. Sweeten, Raubsville, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 593 days.

(21) Appl. No.: 10/641,604

(22) Filed: Aug. 15, 2003

(65) Prior Publication Data

US 2005/0036295 A1 Feb. 17, 2005

(51) Int. Cl.
 *C07C 5/00* (2006.01)
(52) U.S. Cl. ...................... 585/475; 585/906
(58) Field of Classification Search ............... 585/475, 585/906; 502/202
 See application file for complete search history.

(56) References Cited

U.S. PATENT DOCUMENTS

| | | | | |
|---|---|---|---|---|
| 4,029,716 | A | 6/1977 | Kaeding | 260/672 |
| 4,049,573 | A | 9/1977 | Kaeding | |
| 4,067,920 | A | 1/1978 | Kaeding | 260/671 |
| 4,078,009 | A * | 3/1978 | Kaeding | 585/417 |
| 4,097,543 | A | 6/1978 | Haag et al. | 260/672 |
| 4,264,473 | A | 4/1981 | Tu et al. | 252/432 |
| 5,243,117 | A | 9/1993 | Chang et al. | 585/467 |
| 5,567,666 | A * | 10/1996 | Beck et al. | 502/71 |

FOREIGN PATENT DOCUMENTS

| | | |
|---|---|---|
| EP | 0 030 796 | 6/2001 |
| WO | WO 98/14415 | 4/1998 |
| WO | 2005/018806 | 3/2005 |

OTHER PUBLICATIONS

Takahashi, T. et al., "Vapor phase reaction of cyclohexanone oxime over boria modified HSZM-5 zeolites", Canadian Journal of Chemical Engineering, vol. 69, No. 5, Oct. 1991, pp. 1096-1099.
Kim, J.H. et al., "Shape Selectivity of ZSM-5 Type Zeolite for Alkylation of Ethylbenzene with Ethanol", Bulletin of the Chemical Society of Japan, vol. 61, No. 7, Apr. 1988, pp. 1051-1055.
Sayed, Moein et al., "The Effect of Modification with Boron on the Catalytic Activity and Selectivity of HZSM-5", *Journal of Catalysis* 101, pp. 43-55 (1986).
Young, L. B., et al., "Shape Selective Reactions with Zeolite Catalysts, III. Selectivity in Xylene Isomerization, Tolune-Methanol Alkylation, and Toluene Disproportionation over ZSM-5 Zeolite Catalysts", *Journal of Catalysis*, 76, pp. 418-432 (1982).
Kim, John-Ho, et al., "Para-selectivity of zeolites with MFI structure—Difference between disproportionation and alkylation", *Applied Catalysis* A vol. 83 pp. 51-58 (1992).
Sayed, Moein B., et al., "The Effect of Boron on ZSM-5 Zeolite Shape Selectivity and Activity, II. Coincorporation of Aluminum and Boron in the Zeolite Lattice", *Journal of Catalysis* vol. 116, 1-10 (1989).
Ivanova, I. I., et al., "Disproportionation of toluene on modified pentasils", Neftekhimiya, 28(4), pp. 460-467 (1988).
Meshram, Namdeo R., "Selective Toluene Disproportionation Over ZSM-5 Zeolites", J. Chem. Tech. Biotechnol., vol. 37, pp. 111-122 (1987).

* cited by examiner

*Primary Examiner*—Thuan Dinh Dang
(74) *Attorney, Agent, or Firm*—Michael Kerns

(57) ABSTRACT

In a process for preparing a selectivated catalyst composition useful in the disproportionation of toluene, a catalyst comprising an acidic molecular sieve is contacted with a boron compound at a temperature in excess of 500° C.; and the resultant catalyst is then contacted with a medium containing hydrogen ions to at least partially restore the acid activity of the molecular sieve.

26 Claims, No Drawings

SELECTIVATION OF MOLECULAR SIEVE CATALYSTS AND USE THEROF IN HYDROCARBON CONVERSION

FIELD OF THE INVENTION

The present invention relates to the selectivation of molecular sieve catalysts and the use of the selectivated catalysts in shape selective hydrocarbon conversion processes, such as the disproportionation of toluene to para-xylene.

BACKGROUND OF THE INVENTION

Shape-selective catalysis is described, e.g., by N. Y. Chen, W. E. Garwood, and F. G. Dwyer, Shape Selective Catalysis in Industrial Applications, 36, Marcel Dekker, Inc. (1989). Within a pore of the molecular sieve, hydrocarbon conversion reactions such as isomerization, disproportionation, alkylation, and transalkylation of aromatics are governed by constraints imposed by the pore size. Reactant selectivity may occur when a fraction of the feedstock is too large to enter the molecular sieve pores to react, while product selectivity may occur when some of the products cannot leave the molecular sieve pores. Product distributions can also be altered by transition state selectivity in which certain reactions cannot occur because the reaction transition state is too large to form within the molecular sieve pores or cages.

Another type of selectivity results from configurational constraints on diffusion where the dimensions of the molecule approach that of the molecular sieve pore system. A small change in the dimensions of the molecule or the molecular sieve pore can result in large diffusion changes leading to different product distributions. This type of shape-selective catalysis is demonstrated, for example, in selective alkyl-substituted benzene disproportionation to para-dialkyl-substituted benzene.

A representative para-dialkyl-substituted benzene is para-xylene. Typical methods for the production of para-xylene include the methylation of toluene and the disproportionation of toluene over a catalyst under conversion conditions. Such methods may result in the production of a mixture of the three xylene isomers, i.e., para-xylene, ortho-xylene, and meta-xylene. Depending upon the degree of selectivity of the catalyst for para-xylene (para-selectivity) and the reaction conditions, different percentages of para-xylene are obtained. Of the xylene isomers, i.e., ortho-, meta- and para-xylene, para-xylene is of particular value as a large volume chemical intermediate in a number of applications, such as the manufacture of terephthalic acid, which is an intermediate in the manufacturer of polyester.

Various methods are known in the art for increasing the para-selectivity of zeolite catalysts. One such method involves selectivating the catalyst, e.g., ZSM-5, with a selectivating agent. The term "selectivating agent" is used herein to indicate substances which will increase the shape-selectivity (e.g., para-selectivity) of the catalyst. For example, one technique, as disclosed in U.S. Pat. No. 5,243,117, involves treating the catalyst with a selectivating agent containing silicon. This technique usually requires several sequential silicone treatments that can substantially increase the cost of manufacturing the catalyst. Another technique, as disclosed in U.S. Pat. No. 4,097,543, involves the selective disproportionation of toluene in the presence of a catalyst comprising a molecular sieve, e.g., ZSM-5, that contains a controlled amount of carbon coke deposited on the catalyst. This technique requires on-stream selectivation of the catalyst and further selectivations after regeneration of the catalyst. Still another technique involves impregnating the catalyst with oxides that are difficult to reduce, such as those of magnesium, calcium, and/or phosphorus.

SUMMARY OF THE INVENTION

In accordance with the present invention, there is provided a process for preparing a selectivated catalyst. The process comprises: (a) contacting a catalyst comprising an acidic molecular sieve with a boron compound at a temperature greater than 500° C.; and, (b) contacting the catalyst of step (a) with a medium containing hydrogen ions to at least partially restore the acid activity of the molecular sieve.

In another embodiment, the present invention provides a process for the conversion of organic compounds, e.g., hydrocarbons, using the boron-selectivated catalyst prepared by the process described above. Examples of conversion processes that find particular application include the disproportionation of toluene, xylenes isomerization, toluene alkylation with methanol, reformate alkylation with methanol, ethylbenzene isomerization, ethylbenzene dealkylation, shape selective reform, conversion of oxygenates to light olefins, and conversion of oxygenates to aromatics.

DETAILED DESCRIPTION OF THE INVENTION

The present invention concerns incorporating a boron compound into a molecular sieve catalyst formulation, such as by extrusion or impregnation, calcining the boron-containing molecular sieve catalyst at a temperature greater than 500° C., and then contacting the catalyst with a medium containing hydrogen ions to at least partially restore the acid activity of the molecular sieve.

The calcination is conducted at a temperature substantially above the normal calcination temperatures used with molecular sieve catalysts. Although not bound by any theory of operation, it is believed that the high temperature calcination causes the boron compound to react with the molecular sieve crystals from the outside in to leave an amorphous boundary, e.g., coating, on the surface of the crystals. It is also believed that longer calcination times can increase the thickness of this boundary. Subsequent washing of the coated molecular with a medium containing hydrogen ions is believed to remove any unreacted boron compound, which could block the pores, from the molecular sieve. In line with this theory, it is believed that the resulting boundary forms an effective diffusion barrier on the molecular sieve. Regardless of the theory proposed, molecular sieves prepared by the process have one or more of the improved properties which are disclosed herein.

The molecular sieve, which is subjected to the selectivation treatment described herein, is preferably an intermediate pore size molecular sieve. Such intermediate pore size molecular sieves usually have a Constraint Index of between about 1 and about 12. A method for determining Constraint Index is described in U.S. Pat. No. 4,016,218.

Intermediate pore size molecular sieves have a pore size from about 5 to about 7 Å. Examples of such molecular sieves include MWW, MFI, MEL, MFS, MEI, MTW, EUO, MTT, HEU, FER, and TON structure types. These materials are described in "Atlas of Zeolite Framework Types", eds. Ch. Baerlocher, W. H. Meier, and D. H. Olson, Elsevier, Fifth Edition, 2001, which is hereby incorporated by reference. Examples of specific intermediate pore size molecular sieves include ZSM-5, ZSM-11, ZSM-12, ZSM-22, ZSM-23, ZSM-34, ZSM-35, ZSM-38, ZSM-48, ZSM-50, and ZSM-57. The preferred molecular sieve is ZSM-5.

The intermediate pore size molecular sieves will generally be a composition having the following molar relationship:

$$X_2O_3{:}(n)YO_2,$$

wherein X is a trivalent element such as aluminum, iron, boron, and/or gallium and Y is a tetravalent element such as silicon, tin, and/or germanium; and n has a value greater than 12, said value being dependent upon the particular type of molecular sieve. When the intermediate pore size molecular sieve has a MFI structure, n is preferably greater than 10.

When the molecular sieve is an aluminosilicate zeolite, the zeolite will generally have a silica to alumina mole ratio from 10:1 to 700:1 and preferably from 20:1 to 200:1.

When the molecular sieve is a gallosilicate molecular sieve, the molecular sieve usually will be a composition having the following molar relationship:

$$Ga_2O_3{:}ySiO_2$$

wherein y is between about 20 and about 500. The molecular sieve framework may contain only gallium and silicon atoms or may also contain a combination of gallium, aluminum, and silicon.

Preferably, the molecular sieve is a metallosilicate, such as an aluminosilicate, borosilicate, or gallosilicate.

The molecular sieve subjected to the selectivation treatment described herein should have sufficient acidity to provide the catalyst with the activity required for the contemplated organic compound, e.g., hydrocarbon conversion process. An approximate indication of the acid activity of a catalyst is its so-called "alpha value". The alpha test is described in U.S. Pat. No. 3,354,078 and in the Journal of Catalysis, Vol. 4, 522-529 (1965); Vol. 6, 278 (1966); and Vol. 61, 395 (1980), each incorporated herein by reference to that description. The experimental conditions of the alpha test preferably include a constant temperature of 538° C. and a variable flow rate as described in detail in the Journal of Catalysis, Vol. 61, 395 (1980). The present catalysts may have an alpha value greater than 50, e.g., greater than 200, e.g., from about 200 to about 1500.

The molecular sieve, which is subjected to the selectivation treatment described herein, may be combined with a binder material prior to contact with the boron compound. This binder material is preferably an inert, non-alumina binder material, such as a silica binder. Optionally, however, the molecular sieve may be selectivated in the unbound state. Thus, one particular process for introducing the boron compound into molecular sieve is by impregnation, in which the bound or unbound-molecular sieve is allowed to contact a solution of the boron compound in a solvent, such as water. Thereafter, the solvent is removed, such as by evaporation, and the boron-containing molecular sieve is heated to the desired calcination temperature.

An alternative process for contacting the molecular sieve with the boron compound comprises the steps of mulling and then extruding a mixture comprising water, the molecular sieve and a boron compound under conditions sufficient to form an extrudate having an intermediate green strength sufficient to resist attrition during subsequent processing. The extruded mixture is then heated to drive off the water and then react the molecular sieve with the boron compound. If desired, the extruded mixture may undergo intermediate processing, such as, for example, contacting the extruded mixture with an aqueous solution comprising ammonium cations under conditions sufficient to exchange cations in molecular sieve with ammonium cations and calcining the ammonium exchanged extruded mixture under conditions sufficient to generate the hydrogen form of said sieve.

Where the treating boron compound is a liquid, such compound can be in solution in a solvent at the time contact with the molecular sieve is effected. Any solvent relatively inert with respect to the treating compound and the molecular sieve may be employed. Suitable solvents include water and aliphatic, aromatic or alcoholic liquids. Where the boron-containing compound is, for example, trimethylborate, a hydrocarbon solvent such as n-octane may be employed. The boron-containing compound may be used without a solvent, i.e., may be used as a neat liquid.

In addition to the liquid phase contacting processes so far described, the combination of the boron compound with the molecular sieve can be conducted in the gaseous phase. Where the boron-containing compound is in the gaseous phase, such as where gaseous diborane is employed, the treating compound can be used by itself or can be used in admixture with a gaseous diluent inert to the boron-containing compound and the molecular sieve such as nitrogen or helium or with an organic solvent, such as octane.

The catalyst may be preselectivated with boron by single or multiple treatments with the boron compound, each treatment being followed by calcination of the treated material in an oxygen containing atmosphere, e.g., air. For example, the catalyst may be treated at least twice, e.g., at least 3 times, e.g., from 4 to 6 times, with a liquid medium comprising a liquid carrier and at least one boron compound. The liquid carrier may be water, an organic liquid or a combination of water and an organic liquid. Particularly, when the liquid medium comprises an emulsion of the boron compound in water, the liquid medium may also comprise an emulsifying agent, such as a surfactant.

Representative boron-containing compounds, which can be used in the selectivation process of the invention, include boric acid, trimethylborate, boron hydride, boron oxide, boron sulfide, butylboron dimethoxide, butylboronic acid, dimethylboric anhydride, hexamethylborazine, phenylboric acid, triethylborane, tetramethylammonium borohydride, triphenyl boron and allylborate. An embodiment of the invention concerns using boric acid as the boron compound, because of its low acidity and melt characteristics, i.e., boric acid ($H_3BO_3$) at about 150° C. forms boric oxide ($B_2O_3$), which at about 500° C. forms a molten phase.

Prior to contacting the molecular sieve with the boron-containing compound, the catalyst may be dried. Drying can be effected in the presence of air. Elevated temperatures may be employed. However, the temperature should not be such that the crystal structure of the molecular sieve is destroyed.

After contacting with the boron-containing compound, the molecular sieve is calcined by heating to a temperature in excess of 500° C., typically from about 550 to about 800° C., such as at about 650 to about 705° C. (1200 to 1300° F.). By heating at such temperatures, it is believed that the boron compound reacts with the molecular sieve and, upon cooling and solidification, partially blocks the pores of the molecular sieve, thereby creating a diffusion barrier.

When the molecular sieve is preselectivated by a multiple impregnation technique, the molecular sieve is heated after each impregnation to remove the carrier. Following each or the final impregnation, the molecular sieve may be heated at a rate of from about 0.2° C./minute to about 5° C./minute to a temperature greater than 500° C., but below the temperature at which the crystallinity of the molecular sieve is adversely affected. The duration of calcination at the calcination temperature may be from 1 to 24 hours, e.g., from 2 to 6 hours.

The impregnated molecular sieve may be calcined in an inert or oxidizing atmosphere. An example of such an inert atmosphere is a nitrogen, i.e., $N_2$, atmosphere. An example of an oxidizing atmosphere is an oxygen containing atmosphere, such as air. Calcination may take place initially in an inert, e.g., $N_2$, atmosphere, followed by calcination in an oxygen containing atmosphere, such as air or a mixture of air and $N_2$. Calcination should be performed in an atmosphere substantially free of water vapor to avoid undesirable uncontrolled steaming of the molecular sieve. The molecular sieve may be calcined once or more than once following each impregnation. The various calcinations following each impregnation need not be identical, but may vary with respect to the temperature, the rate of temperature rise, the atmosphere and the duration of calcination.

Although the amount of boron incorporated with the molecular sieve will vary, the molecular sieve will usually contain at least about 0.01 percent by weight, and, preferably, at least about 0.5 percent, and most preferably at least 0.8 percent by weight of boron. It is preferred that the amount of boron in the molecular sieve be at least about 1 percent by weight when the same is combined with a binder. The amount of boron can be as high as about 20 percent by weight or more depending on the amount and type of binder present. Preferably, the amount of boron added to the molecular sieve is between about 3.0 and 12.0 percent by weight.

The amount of boron incorporated with the molecular sieve by reaction with a boron-containing compound will depend upon several factors. One of these is the reaction time, i.e. the time that the molecular sieve and the boron-containing source are maintained in contact with each other. With greater reaction times, all other factors being equal, a greater amount of boron is incorporated with the molecular sieve. Other factors upon which the amount of boron incorporated with the molecular sieve is dependent include reaction temperature, concentration of the treating compound in the reaction mixture, the degree to which the molecular sieve has been dried prior to reaction with the boron-containing compound, the conditions of drying of the molecular sieve after reaction of the molecular sieve with the treating compound, and the amount and type of binder incorporated with the molecular sieve.

After selectivation with boron, the catalyst is contacted with a medium containing hydrogen ions to at least partially restore the acid activity of the molecular sieve. The medium employed is conveniently an aqueous medium, such as water or an ammonium hydroxide solution. Preferably, the medium will also contain a chelating agent, such as oxalic acid. Alternatively, the catalyst can be subsequently washed with an aqueous medium containing a chelating agent.

The present invention can impart distinct changes (4-6 orders of magnitude) in diffusion characteristics of the molecular sieve while it retains excellent acid activity. Diffusional resistance for porous crystalline materials is typically reported as the Diffusion Parameter, $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

Preferably, the molecular sieve has a Diffusion Parameter, $D/r^2$, for 2,3-dimethylbutane of less than $1000 \times 10^{-6}$ sec$^{-1}$, when measured at a temperature of 120° C. and a 2,3-dimethylbutane pressure of 60 torr. Further, the selectivated molecular sieve can show about 80% selectivity towards p-xylene versus meta- and ortho-xylene in processing toluene. In addition, the present invention provides a selectivation process, which is permanent, inexpensive and environmentally benign.

The present invention provides a catalyst, which is particularly useful in selective toluene disproportionation, because the catalyst does not require any further modification or selectivation and gives selectivities similar to silicon selectivated catalysts. Further, the present invention provides a catalyst preparation method, which requires fewer steps than a silicon selectivated catalyst, thus providing significant efficiencies and cost savings for manufacture. The present invention also provides a catalyst, which exhibits better yield benefits as compared to a silicon selectivated catalyst, including lower ethylbenzene and $C_9$+ production. Longer process cycles often result from lower $C_9$+ yields in aromatics processes.

The present invention provides a catalyst which is useful in other shape-selective processes such as xylene isomerization and ethylbenzene hydrodealkylation, toluene alkylation with methanol, reformate alkylation with methanol, reformate upgrading, p-ethyltoluene synthesis, p-diethylbenzene synthesis, ethylbenzene isomerization and shape selective reforming. The catalyst also exhibits properties which make it useful in other processes including methanol conversion (e.g., methanol to olefins), fluidized catalytic cracking, enhanced naphtha cracking, pyridine synthesis, paraffin isomerization, lube dewaxing, and cresol isomerization.

In practicing the desired conversion process it may be desirable to combine the molecular sieve with another material resistant to the temperatures and other conditions employed in the conversion process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified molecular sieve include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the molecular sieve employed herein may be composited with a porous matrix material, such as alumina, silica-alumina, silica-magnesia, silica-zirconia, silica-thoria, silica-berylia, silica-titania, as well as ternary compositions, such as silica-alumina-thoria, silicia-alumina-zirconia, silica-alumina-magnesia and silica-magnesia-zirconia. The matrix may be in the form of a cogel. Further, the molecular sieve may be composited with crystalline microporous molecular sieve material. Examples of such materials are disclosed in U.S. Pat. No. 6,008,425, which is hereby incorporated by reference. The relative proportions of molecular sieve and matrix material may vary widely with the sieve content ranging from between about 1 to about 99 percent by weight and more usually in the range of about 5 to about 80 percent by weight of the composite.

Optionally, the present catalyst may contain a hydrogenation/dehydrogenation component. Examples of such optional components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VA metals (i.e., Sb and Bi), and Group VIIB metals (i.e., Mn, Tc and Re). Noble metals (i.e., Pt, Pd, Ir, Rh, Os and Ru) are particular optional hydrogenation/dehydrogenation components. Combinations of catalytic forms of such noble or non-noble metal, such as combinations of Pt with Sn, may be used. The valence state of the metal is preferably in a reduced valence state, e.g., when this component is in the form of an oxide or hydroxide. The reduced valence state of this metal may be attained, in situ, during the course of a reaction, when a reducing agent, such as hydrogen, is included in the feed to the reaction. Preferably, the present catalyst is free of noble metal.

The optional hydrogenation/dehydrogenation component may be incorporated into the catalyst by methods known in the art, such as ion exchange, impregnation or physical admixture. For example, solutions of appropriate metal salts may be contacted with the remaining catalyst components, either before or after selectivation of the catalyst, under conditions sufficient to combine the respective components. The metal containing salt is preferably water soluble. Examples of such salts include chloroplatinic acid, tetrammine-platinum complexes, platinum chloride, tin sulfate and tin chloride.

The amount of optional hydrogenation/dehydrogenation component may be that amount which imparts or increases the catalytic ability of the overall catalyst to catalytically hydrogenate or dehydrogenate an organic compound under sufficient hydrogenation or dehydrogenation conditions. This amount is referred to herein as a catalytic amount. Quantitatively speaking, when the present catalyst comprises a noble metal, it may comprise, for example, from about 0.001 to about 5 wt %, e.g., from about 0.1 to about 2 wt %, of the noble metal.

The conversion can take place in any convenient mode, for example, in fluidized bed, moving bed, or fixed bed reactors depending on the types of process desired.

The selectivated catalyst can be used for a wide variety of organic, e.g., hydrocarbon, conversion processes. Exemplary processes include processes where aromatic compounds are converted to different aromatic compounds. Non-limiting examples of such processes include the following:

(A) The isomerization of dialkyl substituted benzenes, e.g., xylenes. Typical reaction conditions including a temperature from about 230° C. to about 510° C., a pressure of from about 1 atmosphere to about 50 atmospheres, a weight hourly space velocity of from about 0.1 $hr^{-1}$ to about 200 $hr^{-1}$ and a hydrogen/hydrocarbon mole ratio of from 0 (no added hydrogen) to about 100.

(B) The disproportionation of monoalkyl substituted benzenes, e.g., disproportionation of toluene to benzene and xylenes. Typical reaction conditions including a temperature of from about 200° C. to about 760° C., a pressure of from about atmospheric to about 60 atmospheres and a weight hourly space velocity of from about 0.08 $hr^{-1}$ to about 20 $hr^{-1}$.

(C) The alkylation of aromatic compounds, e.g. benzene and $C_7$ and $C_8$ alkylbenzenes, in the presence of an alkylating agent, e.g., olefins, formaldehyde, alkyl halides, and oxygenates, e.g., ethers, and alcohols. Typical reaction condition include a temperature of from about 340° C. to about 500° C., a pressure of from about atmospheric to about 200 atmospheres, a weight hourly space velocity of from about 2 $hr^{-1}$ to about 2000 $hr^{-1}$ and an aromatic hydrocarbon/alkylating agent mole ratio of from about 1/1 to about 20/1.

(D) The transalkylation of aromatic compounds in the presence of polyalkylaromatic compounds. Typical reaction conditions include a temperature of from about 340° C. to about 600° C., a pressure of from about atmospheric to about 200 atmospheres, a weight hourly space velocity of from about 10 $hr^{-1}$ to about 1000 $hr^{-1}$ and an aromatic hydrocarbon/polyalkylaromatic hydrocarbon mole ratio of from about 1/1 to about 16/1.

(E) The dealkylation of alkylaromatic compounds. In the case of ethylbenzene, the ethylbenzene can be converted to benzene and ethane. Typical reaction conditions including a temperature from about 230° C. to about 510° C., a pressure of from about 1 atmosphere to about 50 atmospheres, a weight hourly space velocity of from about 0.1 $hr^{-1}$ to about 200 $hr^{-1}$ and a hydrogen/hydrocarbon mole ratio of from 0 (no added hydrogen) to about 100.

(F) The isomerization of ethylbenzene to form xylenes. Exemplary conditions include a temperature from about 300° C. to about 550° C., a pressure of from about 50 to 500 psig, and a LHSV of from about 1 to about 20.

(G) The isomerization of dialkylnaphthalene, e.g., dimethylnaphthalene, to form a mixture of isomers. Of the dimethylnapthalene isomers, 2,6-dimethylnapthalene is a key intermediate in the production of 2,6-napthalenedicarboxylic acid, a valuable monomer for specialty polyester manufacture. Typical reaction conditions including a temperature from about 230° C. to about 510° C., a pressure of from about 1 atmosphere to about 50 atmospheres, a weight hourly space velocity of from about 0.1 $hr^{-1}$ to about 200 $hr^{-1}$ and a hydrogen/hydrocarbon mole ratio of from 0 (no added hydrogen) to about 100.

(H) The disproportionation of mono-alkyl substituted naphthalenes, e.g., disproportionation of mono-methyl naphthalene to dimethyl-naphthalene and naphthalene.

Exemplary conversion processes also include processes where non-aromatic compounds are converted to aromatic compounds. Non-limiting examples of such processes include the following:

(A) The conversion of light paraffins to aromatics and olefins. Typical reaction conditions include a temperature from about 375° C. to about 760° C. and a pressure from about 10 to about 2000 psig.

(B) The conversion of light olefins to aromatics. Exemplary reaction conditions include a temperature from about 175° C. to about 760° C. and a pressure from about 100 to about 2000 psig (C) The conversion of naphtha, e.g., $C_6$-$C_{10}$, and similar mixtures to highly aromatic mixtures. Thus, normal and slightly branched chained hydrocarbons, preferably having a boiling range above about 40° C., and less than about 200° C., can be converted to products having a substantial higher octane aromatics content. Typical reactions include a temperature in the range of from about 400° C. to 600° C., preferably 480° C. to 550° C., a pressure in the range from atmospheric to 40 bar, and liquid hourly space velocities (LHSV) ranging from 0.1 to 15.

(D) The dehydrogenation of cycloaliphatics having 6 member rings. Typical reaction conditions include a temperature of from about 300° C. to about 700° C., a pressure of from about 0.1 to about 10 atmospheres, a weight hourly space velocity of from about 0.1 $hr^{-1}$ to about 20 $hr^{-1}$.

(E) The conversion of alcohols, e.g., methanol, or ethers, dimethylether, or mixtures thereof to aromatics. Typical reaction conditions include a temperature of from about 275° C. to about 600° C., a pressure of from about 0.5 to about 50 atmospheres, a LHSV of from about 0.5 $hr^{-1}$ to about 50 $hr^{-1}$. Examples of such processes are disclosed in U.S. Pat. No. 4,088,706, which is hereby incorporated by reference.

(F) The dehydration of alcohols to form aromatics, such as the dehydration of cyclohexane-triol to form benzene.

In general, catalytic conversion conditions over the present catalyst will include a temperature of from about 100° C. to about 760° C., a pressure of from about 0.1 atmosphere (bar) to about 200 atmospheres (bar), a weight hourly space velocity of from about 0.08 $hr^{-1}$ to about 2000 $hr^{-1}$ and a hydrogen/organic, e.g., hydrocarbon compound, of from 0 to about 100.

The selectivated catalyst finds particular application in the production of para-xylene via the catalytic disproportionation of toluene. More particularly, this catalyst, under disproportionation conditions, is capable of high conversions of toluene, while at the same time producing a very high proportion of para-xylene among the total of the xylene isomers. However, it will be understood that this catalyst may also be used to catalyze other organic, especially hydrocarbon, conversion reactions.

When the present catalyst is used in a toluene disproportionation reaction, the reaction conditions may include a temperature of about 350° C. to about 550° C., a pressure of about atmospheric to about 5000 psig, a toluene feed rate of about 0.1 to about 20 WHSV, and a hydrogen to toluene mole ratio of about 0.1 to about 20. The hydrogen cofeed serves to suppress catalyst aging, thereby dramatically increasing the cycle length.

The liquid feedstock for the present toluene disproportionation reaction may, optionally, include hydrocarbons other than toluene. Such hydrocarbons include non-aromatic hydrocarbons, such as paraffins and/or cycloparaffins. These non-aromatics may have boiling points close to the boiling point of toluene, which is about 111° C. These non-aromatics are, therefore, difficult to remove from toluene by distillation, and extraction techniques may be needed to separate these toluene coboilers from toluene. The amount of non-aromatics in the fresh feed may be from 0 wt. % to about 3 wt. %, e.g., from about 0.2 wt. % to about 1.5 wt. %. It will also be understood that commercial toluene disproportionation reactions are run by recycling unconverted toluene. The amount of recycled toluene in the feed to the reactor will vary on the amount of toluene conversion per pass. For example, this feed may comprise from about 50 wt. % to about 85 wt. % of recycled toluene. As a result, difficult to remove non-aromatic constituents (e.g., toluene coboilers) may build up in the recycle stream. These toluene coboilers may eventually comprise from about 2 wt. % to about 15 wt. % of the toluene recycle stream. Thus, the total liquid feed to the present disproportionation reactor may comprise both fresh (i.e., make-up) toluene and recycled toluene, and this liquid feed may comprise from 0 wt. % to about 15 wt. % of non-aromatics.

When the present catalyst is used in an ethylbenzene disproportionation reaction, the reaction conditions may include a temperature of about 200° C. to about 600° C., e.g., from about 350° C. to about 540° C.; a pressure of from about atmospheric to about 5000 psig, e.g., from about 100 to about 1000 psig; an ethylbenzene feed rate of from about 0.1 WHSV to about 20 WHSV, e.g., from about 2 WHSV to about 10 WHSV; and a hydrogen to ethylbenzene mole ratio of from about 0.1 to about 20, e.g., from about 2 to about 6.

The present catalysts may be used to convert paraffins from high to low molecular weight hydrocarbons in a dewaxing process. Examples of such dewaxing processes are disclosed in U.S. Pat. Nos. 3,700,585; Re. 28,398; 3,968,024; and 4,181,598, the entire disclosures of which are incorporated herein by reference. Hydrocarbon feeds for dewaxing processes include petroleum stocks that have a freeze point or pour point problem, e.g., petroleum stocks boiling above 350° F. Lubricating oil stocks may be feedstocks to a dewaxing process. The dewaxing may be carried out under either cracking or hydrocracking conditions. Cracking conditions for dewaxing may include a liquid hourly space velocity (LHSV) between about 0.5 and 200, a temperature between about 288° C. (550° F.) and 590° C. (1100° F.), a pressure between about subatmospheric and several hundred atmospheres. Hydrocracking conditions for dewaxing may include a liquid hourly space velocity (LHSV) between about 0.1 and 10, a temperature between about 340° C. (650° F.) and 538° C. (1000° F.), a pressure between about 100 and 3000 psig, and a hydrogen to hydrocarbon mole ratio between about one and 20.

The present catalysts may be used to catalyze the conversion of aliphatic oxygenates to higher molecular weight compounds, e.g., olefins. Such a conversion includes those described, for example, in U.S. Pat. No. 4,476,330, the entire disclosure of which is incorporated herein by reference.

The present catalysts may be used as catalysts in the oligomerization of olefins to form gasoline, distillate, lube oils and/or chemicals. Examples of such oligomerization processes are disclosed in U.S. Pat. Nos. 4,517,399; 4,520,221; 4,547,609; and 4,547,613, the entire disclosures of which are incorporated herein by reference.

The present catalysts may be used to catalyze the conversion of olefins having from 3 to 18 carbon atoms, e.g., propylene, to high viscosity, low pour point lubricating oils. Such a conversion is described, for example, in U.S. Pat. No. 4,517,399, the entire disclosure of which is incorporated herein by reference.

The present catalysts may be used for catalyzing the ethylation of toluene or ethylbenzene to produce a para-ethyl derivative, e.g., para-ethyltoluene. Such a conversion is described, for example, in U.S. Pat. No. 4,086,287, the entire disclosure of which is incorporated herein by reference.

The present catalysts may be used as catalysts in the synthesis of pyridine and substituted pyridines. Process conditions may be selected from those disclosed in U.S. Pat. Nos. 4,675,410 and 4,220,783, the entire disclosures of which are incorporated herein by reference.

The present catalysts may be used as catalysts in the synthesis of caprolactam by the Beckmann rearrangement of cyclohexane oxime. Process conditions may be selected from those disclosed in U.S. Pat. No. 4,359,421, the entire disclosures of which are incorporated herein by reference.

The following examples illustrate the invention:

EXAMPLE 1

A catalyst base material comprising 1/16" extrudates containing 90 wt % ZSM-5 crystal and 10 wt % $SiO_2$ binder was impregnated to 2 wt % $B_2O_3$ from boric acid and then dried at 120° C. (250° F.). Thereafter this process of impregnation and drying was repeated 3 more times for a total of 8 wt % $B_2O_3$ on base catalyst. The dried catalyst was then calcined in flowing air at 700° C. (1300° F.) for 18 hrs. The calcined catalyst was then washed with excess deionized water for 4 days after which it was dried at 120° C. (250° F.) and calcined in flowing air at 540° C. (1000° F.) for 3 hrs.

The selectivated catalyst was characterized for its diffusive properties using 2,3-dimethylbutane as the probe molecule at a temperature of 120° C. and a value of $D/r^2=48\times 10^{-6}$ $m^2$/sec was obtained. The catalyst was also characterized for its acid cracking capability (alpha) at 540° C. (1000° F.) and an alpha value of 130 was obtained. The hexane uptake on the catalyst was measured at 48 mg/g.

EXAMPLE 2

1.67 g of the selectivated catalyst of Example 1 was loaded into a 0.375 inch internal diameter stainless steel cylindrical reactor (with sand as inert packing material). The catalyst was dried in nitrogen, heated up in hydrogen, and held at 400° C. for one hour prior to starting reagent flow. The reagent was 100% toluene. Total reactor effluent was vaporized then analyzed by on-line gas chromatography. The results are given in the following Table 1.

TABLE 1

| | | | | |
|---|---|---|---|---|
| Temperature, ° C. | 400.8 | 399.6 | 440.4 | 441 |
| Temperature, ° F. | 753.44 | 751.28 | 824.72 | 825.8 |
| Pressure, psig | 272 | 268 | 266 | 265 |
| Liquid flowrate ml/hr | 5.77 | 5.77 | 5.77 | 5.77 |
| WHSV, hr-1 | 3.0 | 3.0 | 3.0 | 3.0 |
| $H_2$ flowrate cc/mm | 22.3 | 22.3 | 22.3 | 22.3 |
| $H_2$/HC ratio | 1.0 | 1.0 | 1.0 | 1.0 |
| TOS, hr | 2 | 4 | 6 | 8 |
| Product Composition, Wt % | | | | |
| C5− | 0.30 | 0.34 | 0.81 | 0.96 |
| Benzene | 6.40 | 6.14 | 11.62 | 11.26 |
| Toluene | 84.34 | 84.92 | 74.15 | 74.30 |
| Ethylbenzene | 0.04 | 0.03 | 0.10 | 0.09 |
| Para-xylene | 7.62 | 7.20 | 10.68 | 10.93 |
| Meta-xylene | 0.71 | 0.70 | 1.81 | 1.77 |
| Ortho-xylene | 0.13 | 0.13 | 0.32 | 0.31 |
| Total $C_9$+ | 0.47 | 0.54 | 0.51 | 0.38 |
| Para-xylene selectivity, % | 90.1 | 89.8 | 83.4 | 84.0 |
| Para-xylene purity, % | 89.7 | 89.4 | 82.7 | 83.4 |
| Toluene conversion, % | 15.7 | 15.1 | 25.9 | 25.7 |
| Benzene/xylene (molar) | 1.03 | 1.04 | 1.23 | 1.18 |
| Total xylenes | 8.5 | 8.0 | 12.8 | 13.0 |

| | | | | | | | |
|---|---|---|---|---|---|---|---|
| Temperature, ° C. | 440.6 | 440.2 | 439.9 | 439.9 | 457.6 | 457.7 | 461.8 |
| Temperature, ° F. | 825.08 | 824.36 | 823.82 | 823.82 | 855.68 | 855.86 | 863.24 |
| Pressure, psig | 264 | 264 | 263 | 262 | 262 | 274 | 275 |
| Liquid flowrate ml/hr | 5.77 | 5.77 | 5.77 | 5.77 | 5.77 | 5.77 | 5.77 |
| WHSV, hr-1 | 3.0 | 3.0 | 3.0 | 3.0 | 3.0 | 3.0 | 3.0 |
| $H_2$ flowrate cc/mm | 22.3 | 22.3 | 22.3 | 22.3 | 22.3 | 22.3 | 22.3 |
| $H_2$/HC ratio | 1.0 | 1.0 | 1.0 | 1.0 | 1.0 | 1.0 | 1.0 |
| TOS, hr | 10 | 12 | 14 | 16 | 18 | 20 | 22 |
| Product Comp, Wt % | | | | | | | |
| C5− | 0.80 | 0.73 | 0.61 | 0.65 | 1.01 | 1.30 | 1.21 |
| Benzene | 10.66 | 10.59 | 10.38 | 9.87 | 12.23 | 12.70 | 12.98 |
| Toluene | 75.19 | 75.86 | 76.69 | 76.55 | 71.76 | 71.50 | 70.52 |
| Ethylbenzene | 0.08 | 0.08 | 0.08 | 0.08 | 0.12 | 0.12 | 0.13 |
| Para-xylene | 10.95 | 10.47 | 10.20 | 10.65 | 11.75 | 11.37 | 11.78 |
| Meta-xylene | 1.68 | 1.55 | 1.48 | 1.53 | 2.22 | 2.13 | 2.38 |
| Ortho-xylene | 0.30 | 0.28 | 0.26 | 0.27 | 0.39 | 0.37 | 0.41 |
| Total $C_9$+ | 0.34 | 0.45 | 0.36 | 0.40 | 0.53 | 0.52 | 0.58 |
| Para-xylene selectivity, % | 84.7 | 85.1 | 85.4 | 85.5 | 81.9 | 81.9 | 80.8 |
| Para-xylene purity, % | 84.2 | 84.6 | 84.9 | 85.0 | 81.2 | 81.2 | 80.1 |
| Toluene conversion, % | 24.8 | 24.1 | 23.3 | 23.4 | 28.2 | 28.5 | 29.5 |
| Benzene/xylene (mol.) | 1.12 | 1.17 | 1.18 | 1.08 | 1.16 | 1.24 | 1.21 |
| Total xylenes | 12.9 | 12.3 | 11.9 | 12.5 | 14.3 | 13.9 | 14.6 |

| | | | | | | | |
|---|---|---|---|---|---|---|---|
| Temperature, ° C. | 462.2 | 462 | 462.4 | 462.1 | 462.1 | 462.4 | 462.3 |
| Temperature, ° F. | 863.96 | 863.6 | 864.32 | 863.78 | 863.78 | 864.32 | 864.14 |
| Pressure, psig | 273 | 272 | 267 | 268 | 266 | 266 | 265 |
| Liquid flowrate ml/hr | 5.77 | 5.77 | 5.77 | 5.77 | 5.77 | 5.77 | 5.77 |
| WHSV, hr-1 | 3.0 | 3.0 | 3.0 | 3.0 | 3.0 | 3.0 | 3.0 |
| $H_2$ flowrate cc/mm | 22.3 | 22.3 | 22.3 | 22.3 | 22.3 | 22.3 | 22.3 |
| $H_2$/HC ratio | 1.0 | 1.0 | 1.0 | 1.0 | 1.0 | 1.0 | 1.0 |
| TOS, hr | 24 | 26 | 30 | 32 | 34 | 36 | 38 |

TABLE 1-continued

| Product Comp, Wt % | | | | | | | |
|---|---|---|---|---|---|---|---|
| C5– | 1.55 | 1.66 | 1.35 | 1.53 | 0.98 | 0.94 | 1.18 |
| Benzene | 13.31 | 13.15 | 13.07 | 12.81 | 12.66 | 12.11 | 12.45 |
| Toluene | 70.22 | 70.41 | 70.73 | 71.14 | 72.23 | 72.44 | 71.90 |
| Ethylbenzene | 0.13 | 0.12 | 0.12 | 0.11 | 0.11 | 0.11 | 0.11 |
| Para-xylene | 11.44 | 11.16 | 11.37 | 11.07 | 10.99 | 11.41 | 11.37 |
| Meta-xylene | 2.42 | 2.34 | 2.33 | 2.20 | 2.14 | 2.21 | 2.19 |
| Ortho-xylene | 0.42 | 0.41 | 0.41 | 0.38 | 0.37 | 0.38 | 0.38 |
| Total $C_9$+ | 0.52 | 0.75 | 0.63 | 0.76 | 0.52 | 0.40 | 0.41 |
| Para-xylene selectivity | 80.1 | 80.2 | 80.6 | 81.1 | 81.4 | 81.5 | 81.6 |
| Para-xylene purity, % | 79.4 | 79.6 | 79.9 | 80.4 | 80.8 | 80.8 | 80.9 |
| Toluene conversion, % | 29.8 | 29.6 | 29.3 | 28.9 | 27.8 | 27.6 | 28.1 |
| Benzene/xylene (mol.) | 1.27 | 1.29 | 1.26 | 1.27 | 1.27 | 1.18 | 1.21 |
| Total xylenes | 14.3 | 13.9 | 14.1 | 13.7 | 13.5 | 14.0 | 13.9 |

EXAMPLE 3 (COMPARATIVE)

A silica selectivated catalyst was prepared following the procedure described in U.S. Pat. No. 5,243,117. The preparation was carried out by adding HZSM-5/$SiO_2$ extrudate to a solution of dimethylphenyl polysiloxane (Dow 550) dissolved in an organic solvent and subsequently calcining the selectivated catalyst. The catalyst was treated with 3 additional silicon selectivation treatments using substantially the same procedure.

The silica selectivated catalyst was characterized for its diffusive properties using 2,3-dimethylbutane as the probe molecule at a temperature of 120° C. and a value of $D/r^2=143\times10^{-6}$ $m^2$/sec was obtained. The catalyst was also characterized for its acid cracking capability (alpha) at 540° C. (1000° F.) and an alpha value of 280 was obtained. The hexane uptake on the catalyst was measured at 62.6 mg/g.

The silica selectivated catalyst was tested for the disproportionation of toluene in the same way as in Example 2 and the results, together with those of the boron selectivated of Example 1 at similar toluene conversion, are given in Table 2.

TABLE 2

|  | Example 3 | Example 1 |
|---|---|---|
| Catalyst |  |  |
| Temperature, ° C. | 399 | 462 |
| Temperature, ° F. | 751 | 864 |
| Pressure, psig | 269 | 273 |
| WHSV, hr-1 | 3.0 | 3.0 |
| $H_2$/HC ratio | 1.0 | 1.0 |
| TOS, hr | 20 | 24 |
| Product Comp, Wt % |  |  |
| C5– | 0.78 | 1.55 |
| Benzene | 12.8 | 13.31 |
| Toluene | 70.03 | 70.22 |
| Ethylbenzene | 0.42 | 0.13 |
| Para-xylene | 13.4 | 11.44 |
| Meta-xylene | 1.48 | 2.42 |
| Ortho-xylene | 0.23 | 0.42 |
| Total $C_9$+ | 0.86 | 0.52 |
| Para-xylene selectivity | 88.7 | 80.1 |
| Toluene conversion, % | 30.0 | 29.8 |
| Benzene/xylene (mol.) | 1.15 | 1.27 |
| Total xylenes | 15.1 | 14.3 |

It will be seen from Table 2 that, although the boron selectivated catalyst required a higher temperature to achieve the same toluene conversion as the silica selectivated catalyst, the yields of ethylbenzene and $C_9$+ compounds were expectedly lower with the boron selectivated catalyst.

What is claimed is:

1. A process for the disproportionation of toluene comprising contacting a reaction stream containing toluene, under conversion conditions, with a selectivated catalyst composition prepared by a process comprising the steps of:
   (a) contacting a catalyst comprising an acidic molecular sieve with a boron compound;
   (b) heating the boron-containing catalyst of step (a) at a temperature of about 650° C. to 705° C. to react said boron compound with the surface of the of the molecular sieve to form an amorphous coating on the surface of the acidic molecular sieve; and,
   (c) contacting the catalyst produced in step (b) with a medium containing hydrogen ions to remove unreacted boron compound from the acidic molecular sieve and to at least partially restore the acid activity of the acidic molecular sieve; said acidic molecular sieve having a Diffusion Parameter, $D/r^2$, for 2,3-dimethylbutane of less than $1000\times10^{-6}$ $sec^{-1}$, when measured at a temperature of 120° C. and a 2,3-dimethylbutane pressure of 60 torr.

2. The process recited in claim 1, wherein the contacting of step (a) comprises impregnating the molecular sieve with the boron compound.

3. The process recited in claim 2, wherein the molecular sieve is ZSM-5.

4. The process recited in claim 2, wherein the molecular sieve is an intermediate pore size molecular sieve.

5. The process recited in claim 4, wherein the heating of step (b) is conducted in the presence of oxygen.

6. The process recited in claim 4, wherein the heating of step (b) is conducted in the presence of air.

7. The process recited in claim 4, wherein the medium used in step (c) is an aqueous medium.

8. The process recited in claim 7, wherein the medium used in step (c) is water.

9. The process recited in claim 8, wherein said medium further comprises a chelating agent.

10. The process recited in claim 4, wherein step (a) and said step (b) are repeated at least two times.

11. The process recited in claim 4, wherein said catalyst is dried prior to contacting the molecular sieve with the boron compound.

12. The process recited in claim 4, wherein said boron compound is incorporated into said molecular sieve by extrusion or impregnation.

13. The process recited in claim 4, wherein said molecular sieve is impregnated with the boron compound by: (i) contacting the molecular sieve with the boron compound; (ii) mulling the product of step (i); and (iii) extruding a mixture comprising water and the product of step (ii) under conditions sufficient to form an extrudate.

14. The process recited in claim 4, wherein the molecular sieve has a structure type selected from the group consisting of MWW, MFI, MEL, MFS, MEI, MTW, EUO, MTT, HEU, FER, and TON.

15. The process recited in claim 14, wherein the molecular sieve is an aluminosilicate zeolite.

16. The process recited in claim 4, wherein the molecular sieve is selected from the group consisting of ZSM-5, ZSM-11, ZSM-12, ZSM-22, ZSM-23, ZSM-34, ZSM-35, ZSM-38, ZSM-48, ZSM-50, and ZSM-57.

17. The process recited in claim 16, wherein said catalyst further comprises a hydrogenation/dehydrogenation component.

18. The process recited in claim 16, wherein said catalyst contains at least about 0.01 percent by weight of boron.

19. The process recited in claim 16, wherein said selectivated catalyst composition has an alpha value greater than 50.

20. The process recited in claim 16, wherein said selectivated catalyst composition has an alpha value greater than 200.

21. The process recited in claim 16, wherein said boron compound is selected from the group consisting of boric acid, trimethylborate, boron hydride, boron oxide, boron sulfide, butylboron dimethoxide, butylboronic acid, dimethylboric anhydride, hexamethylborazine, phenylboric acid, triethylborane, tetramethylammonium borohydride, triphenyl boron and allylborate.

22. The process recited in claim 21, wherein the boron compound is boric acid.

23. The process recited in claim 16, wherein said catalyst further comprises a binder.

24. The process recited in claim 23, wherein said binder is silica.

25. The process recited in claim 4, wherein said process produces at least about 80% paraxylene versus the other xylene isomers.

26. The process recited in claim 4, wherein the conversion conditions comprise a temperature in the range of from about 350° C. to about 550° C., at a pressure in the range of from about 1 atmosphere to about 5000 psig and at a weight hourly space velocity of about 0.1 to about 20.

* * * * *